United States Patent [19]

Fox et al.

[11] 4,104,461

[45] Aug. 1, 1978

[54] 2,2'ANHYDRO-β-D-ARABINOFURANO-SYL-5-FLUOROCYTOSINE

[75] Inventors: Jack J. Fox, White Plains, N.Y.; Joseph H. Burchenal, Noroton, Conn.

[73] Assignee: Research Corporation, New York, N.Y.

[21] Appl. No.: 351,704

[22] Filed: Apr. 16, 1973

[51] Int. Cl.$^2$ ............................................. C07H 19/06
[52] U.S. Cl. ..................................... 536/23; 424/180
[58] Field of Search ................. 260/211.5 R; 424/180; 536/23

[56] References Cited

U.S. PATENT DOCUMENTS

| 3,463,850 | 8/1969 | Shen et al. | 260/211.5 R |
| 3,709,874 | 1/1973 | Moffatt et al. | 260/211.5 R |
| 3,792,040 | 2/1974 | Moffatt et al. | 260/211.5 R |
| 3,812,098 | 5/1974 | Moffatt et al. | 260/211.5 R |
| 3,856,777 | 12/1974 | Ishido et al. | 260/211.5 R |

FOREIGN PATENT DOCUMENTS 455,267  2/1970  Japan ............................... 260/211.5 R Primary Examiner—Johnnie R. Brown
Attorney, Agent, or Firm—Omri M. Behr

[57] ABSTRACT

A novel derivative of 1-β-D-arabinofuranose namely the 5-fluorocytosine derivative has been prepared and found to have excellent activity against mouse leukemia.

8 Claims, No Drawings

2,2'-ANHYDRO-β-D-ARABINOFURANOSYL-5-FLUOROCYTOSINE

The invention described herein was made in the course of work under a grant or award from the Department of Health, Education and Welfare.

DESCRIPTION OF THE PRIOR ART

It has been reported that various cytosine and uracil derivatives of 1-β-D-arabinofuranose demonstrate activity against 5-fluorouracil resistant mouse leukemias. (Hereinbelow for purposes of brevity, the moiety 1-β-D-arabinofuranosyl will be abbreviated to ara.)

It was first discovered that ara cytosine was useful against acute myeloblastic leukemia (Carey and Illison, Clin. Res., 13, 337, (1965), Evans, et al., Proc. Soc. Exptl. Biol. Med., 106, 350, (1961), also, ara 5-fluorocytosine (Fox, et al., J. Med. Chem., 9, 101, (1966) and ara 5-fluorouracil (Yung, et al., J. Am. Chem. Soc. 83, 4060 (1961) are active against transplanted mouse leukemias. It has recently been reported (Hoshi, et al., Gann, 62, 145 (1971) that 2,2'-anhydro-ara-cytosine is active at high dosage levels against the mouse leukemia L1210.

SUMMARY OF THE INVENTION 2,2'-Anhydro-1-β-D-arabinofuranosyl-5-fluorocytosine (2,2'-anhydro-ara-5-fluorocytosine) is prepared by the dehydration of 5-fluorocytidine with phosphoryl chloride in dimethylformamide. The resulting product, in the form of the formate salt has substantially higher activity against mouse leukemia L1210 and its mercapto purine resistant variety L1210/6-MP than the related compounds of the prior art at a given dosage level.

In the process of the present invention there is utilized as starting material 5-fluorocytidine which is prepared by reacting 5-fluorocytosine and tri-O-benzoyl-D-ribofuranosylchloride utilizing mercuric cyanide/nitromethane as the condensing agent. In accordance with the method of Yamaoka, et al (J. Org. Chem. 30, 149, 1965); as modified by Watanabe and Fox (J. Heterocyclic Chem., 6, 109 (1969)).

The compound of the present invention, in the form of the formate, shows in vivo activity against leukemia L1210 and the 6-MP-resistant subline L1210/6-MP in mice.

DESCRIPTION OF THE PREFERRED EMBODIMENTS

Anhydro-ara-5-fluorocytosine is synthesized from 5-fluorocytidine by an adaptation of the method of Kikugawa and Ichino, (J. Org. Chem., 37, 284 (1972)). In the process of the present invention there is prepared a dehydrating agent in a suitable polar, nonhydroxylic solvent. Among the preferred solvents are alkyl alkanoylamides, suitably lower alkyl lower alkanoylamides, suitably dilower alkyl lower alkanoylamides, most preferably dimethylformamide. As a dehydrating agent, it is preferred to use a phosphoryl halide suitably phosphoryl chloride.

In the process, dry 5-fluorocytidine is taken up in the solvent of choice, suitably in dimethylformamide, and there is added thereto the previously prepared dehydrating agent. It has been found suitable to use a substantial excess of dehydrating agent. A molar ratio of about 10 moles of dehydrating agent per mole of fluorocytidine has been found suitable.

The reaction mixture is agitated at ambient temperature for from about 1 to about 5 hours, suitably for about 3 hours and then quenched. It has been found desirable to quench the reaction mixture by pouring it over a substantial amount of ice. A ratio of about 100 gms. of ice per gram of 5-fluorocytidine initially charged has been found suitable. The mixture is allowed to stand for about 2 to about 5 hours, suitably for about 3 hours and the thus produced 2,2'-anhydro-ara-5-fluorocytosine in the form of hydrochloride may then be isolated from the reaction mixture.

It has been found desirable to purify the reaction mixture by ion exchange chromatography. Suitably the resin is utilized in the acid form, for example, there may be used a Dowex-50 resin column (pyridinium form).

In the preferred mode of isolation the reaction mixture is applied to a chromatographic column containing the preferred ion exchange resin and the column eluted with water and very dilute, suitably 0.1M pyridinium formate. There are utilized about 5 column volumes of water and 5 column volumes of the pyridinium formate. Chromatography is then continued utilizing a somewhat stronger solution of pyridinium formate (0.5M being preferred). The eluates, suitably about 10 column volumes, are collected, adjusted to a suitable pH, preferably between about 3.5-4.0, most suitably 3.8 with formic acid and the solvents removed, suitably by evaporation under reduced pressure.

The residue is then purified, preferably by trituration with suitable solvents. It has been found that trituration with a halohydrocarbon solvent such as chloroform is suitable. A precipitate is produced which is isolated and further triturated first with the same halohydrocarbon solvent and then with ether. The resulting product is the crystalline formate salt of 2,2'-anhydro-ara-5-fluorocytosine which may be further purified by recrystallization from methanol.

Alternatively, the product may be purified by absorption of the crude formate on an acidic ion exchange resin column such as IRC 50 (H+) followed by elution with formic acid, suitably 0.3M formic acid.

The modes contemplated by the inventor of carrying out the invention include pharmaceutical compositions and processes of administration thereof.

Solutions of the principal active ingredient can be prepared in water or in water suitably diluted with for example, ethanol, glycerin, edible polyols (for example, glycerine, polyethylene glycols, propylene glycol), and the like. Dispersions can be prepared in glycerol, liquid polyethylene glycols, and mixtures thereof, and in oils.

Under ordinary conditions of storage and use, these preparations contain a preservative to prevent the growth of microorganisms.

As stated above, the pharmaceutical compositions can be in forms suited for injectable use which forms include sterile aqueous solutions or dispersions and sterile powders for the extemporaneous preparation of sterile injectable solutions or dispersions. In all cases, the form must be sterile and must be fluid to the extent that easy syringeability exists. It must be stable under the conditions of manufacture and storage and must be preserved against the contaminating action of microorganism such as bacteria and fungi. The basic solvent or dispersion medium can contain water, ethanol, polyols (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersions and by the use of surfactants (for example, a condensation product of ethylene oxide with fatty acids or fatty alcohols, partial esters of fatty acids and a hexitol anhydride, and polyoxyethylene condensation products of the esters). The prevention of the action of microorganisms can be brought about by various antibacterial and antifungal agents, for example, parabens, chlorobutanol, benzyl alcohol, phenol, sorbic acid, themerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the principal active ingredient in the required amount in the appropriate solvent with various of the other ingredients enumerated above, as required, followed by filter sterilization. Generally, dispersions are prepared by incorporating the previously sterilized active ingredient into a sterile vehicle which contains the basic dispersion medium and the required other ingredients from those enumerated above.

In the cases for sterile powders for the preparation of sterile injectable solutions the preferred method of preparation is the freeze-drying technique which yield a powder of the active ingredient plus any additional desired ingredients from a previously sterile-filtered solution thereof. The powders can also be sterilized by the use of a gas, for example, ethylene oxide and subsequently incorporated, with the required additional ingredients and in the proper particle size, into the basic powder for later reconstitution with the desired suspending liquid which, of course, itself must be sterile.

Supplementary active ingredients can be incorporated into the inventive compositions.

It is especially advantageous to formulate the inventive compositions in dosage unit form for ease of administration and uniformity of dosage. Dosage unit form as used in the specification and claims herein refers to physically discrete units suited as unitary dosages for the animal and human subjects to be treated, each unit containing a predetermined quantity of active material calculated to produce the desired therapeutic effect in assocation with the required pharmaceutical carrier. The specifications for the noval dosage unit forms of this invention are dictated by and directly dependent of (a) the unique characteristics of the active material and the particular therapeutic effect to be achieved and (b) the limitations inherent in the art of compounding such an active material for the treatment of disease in living subjects having a diseased condition in which bodily health is impaired as disclosed in detail in this specification, these being features of the present invention.

The dosage of the principal active ingredient for the treatment of the indicated condition depends on the age, weight and condition of the subject being treated, the particular condition and its severity, the particular form of the active ingredient and the route of administration. A dose of from about 1–10 mg/kg may be given singly or in individually smaller doses per day.

The principal active ingredient is compounded for convenient and effective administration in effective amounts with a suitable pharmaceutically acceptable carrier in dosage unit form as hereinbefore described. A unit dosage form can contain the principal active ingredient in amounts ranging from about 1 to about 10 mg/unit. Expressed in proportions the active ingredient is present in from about 0.01 to about 0.1% w./v. of the liquid compositions.

EXAMPLE I

Preparation of 2,2'-anhydro-ara-5-fluorocytosine

There is prepared a mixture of phosphorous oxy chloride (60 g.) and dimethylformamide (200 ml.) which is allowed to stand for 30 minutes. To this mixture is added a solution of dry 5-fluorocytidine (10 g.) in dimethylformamide (40 ml.). The reaction mixture is stirred at ambient temperature for 3 hours and poured over ice (1 Kg.). The aqueous mixture is allowed to stand for 3 hours until U.V. adsorption shows a band at 268nm with disappearance of the original band at 332nm.

The aqueous solution is passed through a Dowex 50 (pyridinium form) column (20 × 9 cm). The column is washed with water (3 l.) and with pyridinium formate aq. (3 l., 0.1M, pH 4.8). The eluates are collected and discarded.

The column is then eluted with pyridinium formate aq. (6 l., 0.5M). The eluates collected, and adjusted to pH 3.8 by addition of formic acid. The eluate is concentrated to a syrup which is triturated with chloroform. The thus formed precipitate is separated by filtration and further triturated successively with chloroform and ether to yield 2,2'-anhydro-ara-5-fluorocytosine (5.7 g, 60%) as the formate.

Crystallization from methanol affords pure material. U.V. $\lambda_{max}^{H_2O}$ 229 and 268 nm ($\epsilon$8700 and 10,900); $\lambda_{min}^{H_2O}$ 244 (4950): $\lambda_{max}^{NHCl}$ 229 and 268 nm ($\epsilon$8400 and 10,600); $\lambda_{min}^{NHCl}$ 244 (4800).NMR(in D$_2$O): $\delta$8.40 and 8.47 (2H, H-6 d, $J_{F,6}$ = 4 Hz, overlapping HCO$_2$D s, respectively), 6.68 d (1H, H-1, J, 1$_{2'}$ = = 6 Hz), 5.63 d (1H, H-2'), ~4.7 (HOD overlapping H-3'), 4.47 m (1H, H-4') and 3.61 (2H, H-5'a, H-5'b, splitting 3 Hz).

Calc'd for C$_9$H$_{10}$FN$_3$O$_4$ . HCOOH: C, 41.50; H, 4.15; N, 14.52; found C, 41.35; H, 4.47; N, 14.54.

Preparation of Starting Material

Tri-O-benzoyl-5-fluorocytidine 21 g.) were stirred in a mixture of benzene-methanol (1:1, 600 ml.). The solution was treated with a sodium methoxide solution (from 1 g. sodium in 100 ml. methanol) and, after stirring for 20 minutes, the solution was passed rapidly through a previously prepared methanol-washed IRC-50 (20–50 mesh), column (15 × 3.5 cm). The column was washed with (300 ml.) methanol and the combined neutral eluates were concentrated to dryness. The yield of crude 5-fluorocytidine was nearly quantitative and gave physical properties similar to those previously reported.

Tri-O-benzoyl-5-fluorocytidine was prepared by condensing equivalent amounts of 5-fluorocytosine with tri-O-benzoyl-D-ribofuranosyl chloride by the mercuric cyanide/nitromethane procedure (Yamaoka, et al, J. Org. Chem. 30, 149, (1965); Watanabe and Fox, J. Heterocyclic Chem., 6, 109 (1969)).

The technique utilized for evaluating the chemotherapeutic activity of the product of the present invention by its ability to prolong the survival time of mice with transplanted leukemia is that of Burchenal, et al, (Cancer 2, 113 (19499). The experiments described here were )). with leukemias L1210 (14) and the 6-MP-resistant subline L1210/6-MP in F$_1$ hybrids of C57BL/6 X DAB/2 cross (BDF$_1$). The 6-MP-resistant subline was chosen because of its increased sensitivity to ara-C and its derivatives since these were in short supply. Since then, experiments with single i.p. and p.o. doses of anhydro-ara-5-fluorocytosine have been repeated with the straight line of L1210 and have shown similar results. With leukemia L1210/6-mercaptopurine no increase in survival time is seen with any tolerated doses of 6-mercaptopurine.

One million leukemic cells suspended in 0.9% NaCl solution were inoculated i.p. into each animal, producing an ascitic leukemia which later progressed to a generalized disease. In some experiments, 250,000 cells were inoculated intracerebrally. The mice were divided into groups of 10 animals each, and the treatment was initiated 1 to 2 days after the inoculation with leukemic cells and continued once daily to a total of 5 doses, unless otherwise noted.

All compounds were dissolved in 0.9% NaCl solution or distilled water or suspended in carboxymethyl cellulose in 0.9% NaCl solution and injected i.p. or given p.o. by intubation in mice fasted for the previous 16 hours. All mice were autopsied at death, and survivors were sacrificed and autopsied at 50 days.

Results

At daily doses of 200 to 300 mg/kg anhydro-ara-5-fluorocytosine caused significant prolongation of survival time in mice inoculated with leukemia L1210 as well as with its mercaptopurine-resistant variant L1210/6-mercaptopurine. At approximately comparably toxic daily doses anhydro-ara-5-fluorocytosine was more active than ara-cytosine, ara-5-fluorocytosine, anhydro-ara-cytosine ("cyclocytidine"), or ara-fluorouracil.

In contrast to ara-cytosine which is less toxic and less effective by a single dose than by daily administration and relatively ineffective when administered p.o. anhydro-ara-5-fluorocytosine is active as a single i.p. or p.o. does of 1500 mg/kg 24 to 48 hours after the inoculation of the leukemic calls, even though previous studies have shown that it is tolerated in normal BDF$_1$ mice at a much larger total dose when given 750 mg/kg i.p. daily for 5 days. The original experiments with anhydro-ara-5-fluorocytosine were done in mice previously fasted for 16 hours, but more recent experiments have shown it to be almost equally active orally in nonfasted mice. It is also active as a single i.p. or p.o. dose in mice with intracerebrally inoculated leukemia L1210 and compares favorably with the known CNS active drug, 1,3-bis(2-chloroethyl)-1-nitrosourea.

We claim:

1. 2,2'-anhydro-1-($\beta$-D-arabinofuranosyl)-5-fluorocytosine and hydrochloride and formate salts thereof.

2. 2,2'-anhydro-1-($\beta$-D-arabinofuranosyl)-5-fluorocytosine formate.

3. In the process of synthesizing 2,2'-anhydro-1-($\beta$-D-arabinofuranosyl)-5-fluorocytosine the step of reacting 5-fluorocytidine with a polar non hydroxylic dehydrating agent in the presence of an alkanoyl amide.

4. The process of claim 3 wherein the dehydrating agent is phosphoryl chloride in the presence of dimethyl formamide.

5. The process of synthesizing the compound of claim 2 which comprises
   a. reacting 5-fluorocytidine with a polar non-hydroxylic phosphorylhalide dehydrating agent,
   b. quenching the reaction mixture with an aqueous quench,
   c. absorbing the product of step (b) in an ion exchange resin in acidic state,
   d. sequentially eluting said resin with
      i. water
      ii. 0.1M pyridinium formate
      iii. 0.5M pyridinium formate
   e. acidifying the eluate of step (d) (iii) with formic acid, and
   f. removing the solvent.

6. The process of claim 5 comprising the additional step of titurating the residue of step (f) with a halohydrocarbon to yield the desired product in crystalline form.

7. The process of claim 5 comprising the additional step of triturating the residue of step (f) with chloroform to yield the desired product in crystalline form.

8. 2,2'-anhydro-1-($\beta$-D-arabinofuranosyl)-5-fluorocytosine hydrochloride.

* * * * *